(12) United States Patent
Kwon et al.

(10) Patent No.: US 11,993,566 B2
(45) Date of Patent: May 28, 2024

(54) HYDROFORMYLATION METHOD

(71) Applicant: LG CHEM, LTD., Seoul (KR)

(72) Inventors: Yonghyun Kwon, Daejeon (KR); Hyunseok Nam, Daejeon (KR); Jihoon Kim, Daejeon (KR); Jangkeun Cho, Daejeon (KR); Daeheung Choi, Daejeon (KR)

(73) Assignee: LG Chem, Ltd., Seoul (KR)

( * ) Notice: Subject to any disclaimer, the term of this patent is extended or adjusted under 35 U.S.C. 154(b) by 303 days.

(21) Appl. No.: 17/641,744

(22) PCT Filed: Jul. 26, 2021

(86) PCT No.: PCT/KR2021/009635
§ 371 (c)(1),
(2) Date: Mar. 9, 2022

(87) PCT Pub. No.: WO2022/025562
PCT Pub. Date: Feb. 3, 2022

(65) Prior Publication Data
US 2022/0306561 A1   Sep. 29, 2022

(30) Foreign Application Priority Data
Jul. 30, 2020   (KR) .......................... 10-2020-0095240

(51) Int. Cl.
*C07C 45/50* (2006.01)
*B01J 31/18* (2006.01)
*B01J 31/22* (2006.01)

(52) U.S. Cl.
CPC ............. *C07C 45/50* (2013.01); *B01J 31/185* (2013.01); *B01J 31/2208* (2013.01); *B01J 2231/321* (2013.01); *B01J 2531/822* (2013.01); *B01J 2531/827* (2013.01); *B01J 2531/845* (2013.01)

(58) Field of Classification Search
CPC ..... C07C 45/50; B01J 31/185; B01J 31/2208; B01J 2231/321
See application file for complete search history.

(56) References Cited

U.S. PATENT DOCUMENTS

| | | |
|---|---|---|
| 4,288,380 A | 9/1981 | Billig et al. |
| 4,528,403 A | 7/1985 | Tano et al. |
| 4,711,968 A | 12/1987 | Oswald et al. |
| 5,817,883 A | 10/1998 | Briggs et al. |
| 2008/0154067 A1 | 6/2008 | Liu et al. |
| 2010/0044628 A1 | 2/2010 | Brammer |
| 2013/0324767 A1 | 12/2013 | Norman et al. |

FOREIGN PATENT DOCUMENTS

| | | |
|---|---|---|
| CN | 109453816 A | 3/2019 |
| EP | 0028892 A1 | 5/1981 |
| EP | 0071281 B1 | 6/1986 |
| JP | 2583546 B2 | 2/1997 |
| JP | 10-273465 A | 10/1998 |
| JP | 2002500620 A | 1/2002 |
| JP | 2010523588 A | 7/2010 |
| JP | 2015-523979 A | 8/2015 |
| KR | 1998-701462 A | 5/1998 |
| KR | 10-2002-0046892 A | 6/2002 |
| KR | 10-2009-0092281 A | 8/2009 |
| KR | 10-2015-0015904 A | 2/2015 |
| WO | 96/22266 A1 | 7/1996 |

OTHER PUBLICATIONS

Behr et al., "Selective hydroformylation-hydrogenation tandem reaction of isoprene to 3-methylpentanal," Dalton Transactions., vol. 40, pp. 11742-11747 (2011).

*Primary Examiner* — Sikarl A Witherspoon
(74) *Attorney, Agent, or Firm* — Bryan Cave Leighton Paisner LLP

(57) ABSTRACT

A hydroformylation method including preparing an aldehyde by reacting a raw-C5 feed with a synthetic gas in the presence of a catalyst composition.

8 Claims, No Drawings

HYDROFORMYLATION METHOD

CROSS-REFERENCE TO RELATED APPLICATIONS

This application is a U.S. national stage of international Application No. PCT/KR2021/009635, filed on Jul. 26, 2021, and claims priority to and the benefits of Korean Patent Application No. 10-2020-0095240, filed with the Korean Intellectual Property Office on Jul. 30, 2020, the entire contents of which are incorporated by reference as if fully set forth herein.

FIELD

The present application relates to a method for hydroformylation.

BACKGROUND

A hydroformylation reaction, which includes reacting various olefins with carbon monoxide (CO) and hydrogen ($H_2$), commonly referred to as a synthetic gas, in the presence of a homogeneous organometal catalyst and a ligand to produce a linear (normal) and branched (iso) aldehyde having the number of carbon atoms increased by one was first discovered by Otto Roelen of Germany in 1938.

The hydroformylation reaction, generally known as an oxo reaction, is industrially very important in a homogeneous catalyst reaction, and various aldehydes comprising alcohol derivatives are produced through the oxo process and consumed worldwide.

Various aldehydes synthesized through the oxo reaction are sometimes oxidized or hydrogenated after a condensation reaction such as an aldol condensation, and modified to various acids and alcohols comprising a long alkyl group. Particularly, a hydrogenated alcohol of an aldehyde produced by such an oxo reaction is referred to as an oxo-alcohol, and the oxo-alcohol is widely used industrially as solvents, additives, raw materials of various plasticizers, synthetic lubricants, and the like.

Catalysts currently used in the oxo process are mainly of the cobalt (Co) and rhodium (Rh) series, and normal/iso selectivity (ratio of linear (normal) to branched (iso) isomers) of an aldehyde produced using these catalysts varies depending on the types of ligand used and operating conditions. Currently, 70% or more of oxo plants around the world are adopting a low pressure oxo process using a rhodium-based catalyst.

As a central metal of the oxo catalyst, iridium(Ir), ruthenium(Ru), osmium(Os), platinum(Pt), palladium (Pd), iron (Fe), nickel (Ni), and the like, may be used in addition to cobalt (Co) and rhodium (Rh). However, these metals are known to exhibit catalytic activity in the order of Rh>>Co>Ir, Ru>Os>Pt>Pd>Fe>Ni, and the like, and accordingly, most processes and studies are focused on rhodium and cobalt.

As the ligand, phosphine ($PR_3$, where R is $C_6H_5$, or n-$C_4H_9$), phosphine oxide (O=P($C_6H_5$)$_3$), phosphide, amine, amide, isonitrile, and the like, may be used.

The hydroformylation reaction may be conducted continuously, semi-continuously or batch-wise, and a typical hydroformylation reaction process is a gas or liquid recirculation system. In the hydroformylation reaction, it is important to increase reaction efficiency by allowing starting materials formed in liquid and gaseous phases to smoothly contact each other. For this purpose, a continuous stirred tank reactor (CSTR), which stirs components in liquid and gaseous phases in the reactor to bring them evenly in contact with each other, has been mainly used in the art.

An existing hydroformylation process has two limitations as follows.

The first disadvantage of an existing hydroformylation process is high unit costs of raw materials. Propylene, a raw material of an octanol process that is a typical hydroformylation process, is in high demand as a raw material for other polymers such as polypropylene, and the price continues to rise. The second disadvantage of an existing hydroformylation process is that concentrations of reaction materials introduced to a batch-type reaction are low and a concentration of a solvent is high. A solvent used in a hydroformylation process performs an important role of helping reaction materials in liquid and gaseous phases to come in contact with a catalyst. In most literature, a hydroformylation process is described as including a process of introducing small amounts of reaction materials and introducing a very large amount of solvent to obtain high activity. However, a problem with such a process is increasing raw material costs and solvent separating costs. Accordingly, studies for resolving the problems of an existing hydroformylation process described above have been required in the art.

SUMMARY

The present application is directed to providing a method for hydroformylation.

An exemplary embodiment of the present application provides a method for hydroformylation, the method comprising preparing an aldehyde by reacting a raw-C5 feed with a synthetic gas in the presence of a catalyst composition, wherein the catalyst composition for a hydroformylation reaction comprises a phosphorous-based ligand, a transition metal compound represented by the following Chemical Formula 1 and a solvent, the solvent comprises one or more types of tetraethylene glycol dimethyl ether (TEGDME), 1,2,4-trimethylbenzene and cumene, and the raw-C5 feed has a total weight ratio of less than 1,000 and the solvent has a total weight ratio of 500 or greater, based on a total weight of the transition metal compound:

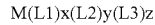  [Chemical Formula 1]

in Chemical Formula 1,

M is rhodium (Rh), cobalt (Co), iridium (Ir), ruthenium (Ru), iron (Fe), nickel (Ni), palladium (Pd), platinum (Pt) or osmium (Os), L1, L2 and L3 are the same as or different from each other, and each independently hydrogen, carbonyl (CO), cyclooctadiene, norbornene, chlorine, triphenylphosphine (TPP) or acetylacetonato (AcAc), and x, y and z are each independently an integer of 0 to 5, and x, y and z are not 0 at the same time.

According to an exemplary embodiment of the present application, a raw-C5 feed, a product of a naphtha cracking center (NCC) process, can be directly used in a hydroformylation reaction process. Accordingly, an exemplary embodiment of the present application is effective in saving operating costs and investment costs compared to existing technologies in the art.

In addition, according to an exemplary embodiment of the present application, an olefin conversion ratio in the raw-C5 feed can be enhanced by including one or more types of tetraethylene glycol dimethyl ether (TEGDME), 1,2,4-trimethylbenzene and cumene as a solvent, and by using a specific weight ratio of a transition metal compound, the solvent and the raw-C5 feed during the hydroformylation step.

DETAILED DESCRIPTION

Hereinafter, the present specification will be described in more detail.

In the present specification, a description of one member being placed "on" another member comprises not only a case of the one member being in contact with the another member but a case of still another member being present between the two members.

In the present specification, a description of a certain part "comprising" certain constituents means capable of further comprising other constituents, and does not exclude other constituents unless particularly stated on the contrary.

As described above, studies capable of resolving problems of an existing hydroformylation process described above have been required in the art.

Aldehydes used for making various alcohol and amine materials are generally synthesized through a hydroformylation process of olefins, and development of an economical hydroformylation process is very important for commercialization of aldehyde production. Raw-C5, one of products of a naphtha cracking center (NCC) process, is traded at a low price and has a high olefin content of 40% by weight to 50% by weight. Therefore, this material has a high economic effect when converted to an aldehyde through a hydroformylation process. However, when several types of olefins with different reaction characteristics (internal monoene, terminal monoene, diene and the like) are mixed, as in raw-C5, it is difficult to effectively produce an aldehyde under a single catalyst system, and an analysis on reaction results is difficult as well. Accordingly, there have been no related studies.

In view of the above, the present application is directed to providing a method for hydroformylation capable of saving operating costs and investment costs compared to existing technologies in the art and enhancing a conversion ratio of olefins by minimizing an amount of introduced solvent while using a raw-C5 feed.

A method for hydroformylation according to an exemplary embodiment of the present application comprises a step of preparing an aldehyde by reacting a raw-C5 feed with a synthetic gas in the presence of a catalyst composition, wherein the catalyst composition for the hydroformylation reaction comprises a phosphorous-based ligand, a transition metal compound represented by Chemical Formula 1 and a solvent, the solvent comprises one or more types of tetraethylene glycol dimethyl ether (TEGDME), 1,2,4-trimethylbenzene and cumene, and the raw-C5 feed has a total weight ratio of less than 1,000 and the solvent has a total weight ratio of 500 or greater based on a total weight of the transition metal compound.

In one embodiment of the present application, the raw-C5 feed is a product of a naphtha cracking center (NCC) process, and the raw-C5 feed comprises a mixture of terminal monoene, internal monoene and diene.

In an external embodiment of the present application, specific components of the raw-C5 feed are shown in the following Table 1:

TABLE 1

| Components of Raw-C5 Feed | | Content (wt %) |
|---|---|---|
| C5 Hydrocarbon | C5 Paraffin | 36 to 42 |
| C5 Olefin | C5 Terminal Monoene | 10 to 16 |
| | C5 Internal Monoene | 2 to 8 |
| | C5 Diene | 23 to 29 |
| Other Components (C4, C6, C7, C8, C9 Hydrocarbon and the like) | | 5 to 29 |
| Total | | 100 |

In an exemplary embodiment of the present application, the C5 terminal monoene may comprise 1-pentene, 2-methyl-1-butene, 3-methyl-1-butene, cyclopentene, and the like. In addition, the C5 internal monoene may comprise 2-pentene, 2-methyl-2-butene, and the like. In addition, the C5 diene may comprise isoprene, 1,3-pentadiene, 1,4-pentadiene, 2-methyl-1-buten-3-yne, and the like.

In an exemplary embodiment of the present application, a content of the diene may be 30% by weight or greater, from 40% by weight to 80% by weight, or from 45% by weight to 75% by weight based on a total weight of the mixture of terminal monoene, internal monoene and diene. Having a diene content of less than 30% by weight based on a total weight of the mixture of terminal monoene, internal monoene and diene is not preferred because the content of the internal monoene having relatively low reactivity increases resulting in a decrease in the olefin conversion ratio of the raw-C5 feed.

In an exemplary embodiment of the present application, the phosphorous-based ligand may comprise one or more types of 1,2-bis(diphenylphosphino)ethane, 4,5-bis(diphenylphosphino), triphenylphosphine and 6,6'-[(3,3'-di-tert-butyl-5,5'-dimethoxy-1,1'-biphenyl-2,2'-diyl)bis(oxy)]bis (dibenzo[d,f][1,3,2]dioxaphosphephine).

In an exemplary embodiment of the present application, the transition metal compound may comprise one or more types of cobalt carbonyl [$Co_2(CO)_8$], acetylacetonatodicarbonyl rhodium [$Rh(AcAc)(CO)_2$], acetylacetonatocarbonyl triphenylphosphine rhodium [Rh(AcAc)(CO)(TPP)], hydridocarbonyl tri(triphenylphosphine)rhodium [$HRh(CO)(TPP)_3$], acetylacetonatodicarbonyl iridium [$Ir(AcAc)(CO)_2$], hydridocarbonyl tri(triphenylphosphine) iridium [$HIr(CO)(TPP)_3$] and chloro(1,5-cyclooctadiene) rhodium [$Rh(COD)Cl_2$].

In an exemplary embodiment of the present application, the solvent may comprise one or more types of tetraethylene glycol dimethyl ether (TEGDME), 1,2,4-trimethylbenzene and cumene. Particularly, the TEGDME has a boiling point of 257.0° C. and has a large boiling point difference of 117° C. to 137° C. with a C6 aldehyde (boiling point: 120° C. to 140° C.) produced after the hydroformylation step. Accordingly, the solvent is readily separated through a distillation process after the hydroformylation step, and therefore, using the TEGDME is more preferred.

In an exemplary embodiment of the present application, the raw-C5 feed has a total weight ratio of less than 1,000 and the solvent has a total weight ratio of 500 or greater based on a total weight of the transition metal compound. In addition, in an exemplary embodiment of the present application, the raw-C5 feed preferably has a total weight ratio of greater than or equal to 50 and less than 1,000 and the solvent preferably has a total weight ratio of 500 to 1,200 based on a total weight of the transition metal compound. In addition, the raw-C5 feed more preferably has a total weight ratio of greater than or equal to 100 and less than or equal to 900 and the solvent more preferably has a total weight ratio of 500 to 1,000 based on a total weight of the transition metal compound. Economic feasibility of the hydroformylation process increases as the raw-C5 feed has a large weight ratio and the solvent has a small weight ratio with respect to a weight of the transition metal compound. However, when the solvent has a total weight ratio of less than 500 based on a total weight of the transition metal compound, the transition metal compound is not sufficiently dissolved, thereby failing to function as a catalyst. As a result, the olefin conversion ratio may be low. In addition, when the solvent has a total weight ratio of greater than 1,000 based on a total weight of the transition metal compound, the transition metal compound is sufficiently dissolved and catalytic activity may be achieved, however, the raw-C5 feed having a very high total weight ratio of 1,000 or greater is not preferred because the relative concentration of the catalyst is low, and the limited amount of catalyst results in insufficient olefin conversion.

In an exemplary embodiment of the present application, the hydroformylation step may be conducted at a reaction temperature of 90° C. or higher, may be conducted at a reaction temperature of 90° C. to 120° C., and may be conducted at a reaction temperature of 90° C. to 110° C. In addition, in an exemplary embodiment of the present application, the hydroformylation step may be conducted at a reaction pressure of 15 bar or greater, may be conducted at a reaction pressure of 20 bar to 60 bar, and may be conducted at a reaction pressure of 20 bar to 50 bar.

When the hydroformylation step has a reaction temperature of lower than 90° C., energy required for the reaction is not sufficiently supplied, and conversion of olefin molecules having low reactivity such as internal monoene or diene may slowly occur or hardly occur. In addition, even with terminal monoene, the reaction time required for conversion is too long, and production efficiency may decrease. In addition, the hydroformylation step having a reaction temperature of higher than 120° C. is not preferred because the catalyst may not function normally due to thermal decomposition of the ligand molecule.

When the hydroformylation step has a reaction pressure of 15 bar or greater, the equivalent of the synthetic gas is sufficiently high with respect to the olefin, which allows the hydroformylation reaction equilibrium to create a condition advantageous for a forward reaction. In addition, C5 olefin molecules having a low boiling point exist in a liquid phase even at high temperatures, which may be advantageous for contact with the catalyst in the reaction solution. In addition, when the hydroformylation step has a reaction pressure of less than 15 bar, conversion of olefin molecules having low reactivity, such as internal monoene or diene, may slowly occur or hardly occur. In addition, the hydroformylation step having a reaction pressure of greater than 60 bar is not preferred because, although it does not cause problems in the reaction, investment costs such as strengthening a reactor for a high pressure process may be additionally incurred, and risks of a high pressure process may increase.

In the hydroformylation step of an exemplary embodiment of the present application, a molar ratio of the raw-C5 feed:the synthetic gas may be from 95:5 to 5:95.

In an exemplary embodiment of the present application, the synthetic gas comprises carbon monoxide and hydrogen, and a molar ratio of the carbon monoxide:the hydrogen may be from 5:95 to 70:30, and from 40:60 to 60:40. When satisfying the molar ratio of the carbon monoxide:the hydrogen, the olefin conversion ratio in the raw-C5 feed may be further enhanced.

Hereinafter, the present application will be described in detail with reference to examples in order to specifically describe the present application. However, examples according to the present application may be modified to various different forms, and the scope of the present application is not construed as being limited to the examples described below. Examples of the present application are provided in order to more fully describe the present application to those having average knowledge in the art.

EXAMPLES

Example 1

A C5 stream solution (10 g) collected from the Daesan NCC plant of LG Chem, a catalyst precursor, a ligand and a solvent were mixed in a fixed ratio and introduced into a pressure reactor (capacity:500 mL). 0.1 g of Rhacac(CO)$_2$ was used as the catalyst precursor, 2 g of 1,2-bis(diphenylphosphino)ethane (DPPE) was used as the ligand, and 100 g of tetraethylene glycol dimethyl ether (TEGDME) was used as the solvent. Components of the C5 stream solution are as shown in Table 1.

Inside the reactor was purged with nitrogen while stirring the reaction solution at 1,000 rpm. When the purging was completed, the temperature inside the reactor was raised to 100° C. After reaching the reaction temperature, a synthetic gas (CO/H$_2$=1/1) was introduced into the reactor at 40 bar to initiate a hydroformylation reaction. After maintaining the hydroformylation reaction conditions for 12 hours, the reactor was cooled to room temperature, and the gas inside the reactor was removed to finish the reaction.

Examples 2 to 6 and Comparative Examples 1 to 7

Reactions were performed in the same manner as in Example 1 except for using the solvents, the amounts of the introduced solvents and the amounts of the introduced C5 stream solutions as described in Table 2:

TABLE 2

| | Solvent | Amount of Introduced C5 Stream | Amount of Introduced Solvent | A | B |
|---|---|---|---|---|---|
| Example 1 | TEGDME | 10 | 100 | 100 | 1,000 |
| Example 2 | Pseudocumene | 10 | 100 | 100 | 1,000 |
| Example 3 | Cumene | 10 | 100 | 100 | 1,000 |
| Example 4 | TEGDME | 75 | 50 | 750 | 500 |
| Example 5 | TEGDME | 50 | 50 | 500 | 500 |
| Example 6 | TEGDME | 90 | 50 | 900 | 500 |
| Comparative Example 1 | Benzene | 10 | 100 | 100 | 1,000 |
| Comparative Example 2 | TEXANOL | 10 | 100 | 100 | 1,000 |
| Comparative Example 3 | TEGDME | 100 | 100 | 1,000 | 1,000 |
| Comparative Example 4 | TEGDME | 100 | 50 | 1,000 | 500 |
| Comparative Example 5 | TEGDME | 50 | 25 | 500 | 250 |

TABLE 2-continued

| Solvent | | Amount of Introduced C5 Stream | Amount of Introduced Solvent | A | B |
|---|---|---|---|---|---|
| Comparative Example 6 | TEGDME | 50 | 0 | 500 | 0 |
| Comparative Example 7 | TEGDME | 50 | 40 | 500 | 400 |

A: total weight ratio of C5 stream with respect to total weight of transition metal compound
B: total weight ratio of solvent with respect to total weight of transition metal compound
TEGDME: tetraethylene glycol dimethyl ether
Pseudocumene: 1,2,4-trimethylbenzene
Cumene: isopropylbenzene
TEXANOL: 2,2,4-trimethyl-1,3-pentanediol monoisobutyrate Experimental Example After completing the reactions according to the examples and the comparative examples, each of the reaction solutions was collected, and olefin conversion ratio and aldehyde selectivity were calculated through gas chromatography (GC). The results are shown in Table 3.

The olefin conversion ratio was calculated through the total consumption ratio, by measuring the amount of C5 olefins present in the raw-C5 feed before and after the reaction. In addition, the aldehyde selectivity was calculated as the amount of total C6 aldehydes produced after the reaction with respect to the total consumption of C5 olefins present in the raw-C5 feed.

Olefin conversion ratio (%)=[(number of moles of reacted C5 olefins)/(number of moles of C5 olefins present in supplied raw-C5 feed)]×100

Aldehyde selectivity (%)=[(number of moles of produced C6 aldehydes)/(number of moles of reacted C5 olefins)]×100

<Condition of GC Analysis>
1) Column: HP-1 (L: 30 m, ID: 0.32 mm, film: 1.05 m)
2) Injection volume: 1 μl
3) Inlet temp.: 250° C., pressure: 6.92 psi, total flow: 64.2 ml/min, split flow: 60 ml/min, spilt ratio: 50:1
4) Column flow: 1.2 m/min
5) Oven temp.: 50° C./3 min–10° C./min–280° C./41 min (total 67 mins)
6) Detector temp.: 300° C., H2: 35 ml/min, air: 300 ml/min, He: 20 ml/min
7) GC model: Agilent 6890

TABLE 3

| | Olefin Conversion Ratio (%) | Aldehyde Selectivity (%) |
|---|---|---|
| Example 1 | 78.1 | 99.1 |
| Example 2 | 79.5 | 64.2 |
| Example 3 | 75.7 | 86.6 |
| Example 4 | 75.0 | 79.8 |
| Example 5 | 73.9 | 72.0 |
| Example 6 | 66.8 | 70.1 |
| Comparative Example 1 | 32.7 | 40.0 |
| Comparative Example 2 | 10.4 | 17.3 |
| Comparative Example 3 | 10.6 | 93.5 |
| Comparative Example 4 | 8.1 | 36.4 |
| Comparative Example 5 | 20.0 | 37.9 |
| Comparative Example 6 | 13.3 | 51.8 |
| Comparative Example 7 | 64.3 | 58.1 |

For Examples 1 to 6, superior olefin conversion ratio and aldehyde selectivity were achieved when using TEGDME, 1,2,4-trimethylbenzene or cumene as the solvent compared to using benzene or TEXANOL as the solvent as in Comparative Examples 1 and 2.

In addition, for Comparative Examples 3 to 7, the hydroformylation reaction did not proceed well when the total weight ratio of the raw-C5 feed and the total weight ratio of the solvent were not satisfied based on the total weight of the transition metal compound of the present application.

Particularly, as shown by the results of Comparative Example 4, the olefin conversion ratio and aldehyde selectivity rapidly decreased when the total weight ratio of the C5 stream with respect to the total weight of the transition metal compound was 1,000 or greater. In addition, as shown by the results of Comparative Example 3, reaction activity was not secured when the total weight ratio of the C5 stream with respect to the total weight of the transition metal compound was 1,000 or greater even when the total weight ratio of the solvent with respect to the total weight of the transition metal compound was 1,000 or greater. In addition, as shown by the results of Comparative Examples 5 to 7, the reaction activity was not secured when the total weight ratio of the solvent with respect to the total weight of the transition metal compound was less than 500.

Accordingly, the raw-C5 feed, a product of a naphtha cracking center (NCC) process, may be directly used in a hydroformylation reaction process according to an exemplary embodiment of the present application. As a result, an exemplary embodiment of the present application is effective in saving operating costs and investment costs compared to existing technologies in the art.

In addition, according to an exemplary embodiment of the present application, an olefin conversion ratio in the raw-C5 feed may be enhanced by comprising one or more types of tetraethylene glycol dimethyl ether (TEGDME), 1,2,4-trimethylbenzene and cumene as the solvent, and by using a specific weight ratio of the transition metal compound, the solvent and the raw-C5 feed during the of hydroformylation step.

The invention claimed is:
1. A hydroformylation method, the method comprising:
reacting a raw-C5 feed with a synthetic gas in the presence of a catalyst composition to produce an aldehyde, wherein the catalyst composition comprises a phosphorous-based ligand, a transition metal compound of Chemical Formula 1, and a solvent:

[Chemical Formula 1]

$$M(L1)x(L2)y(L3)z$$

wherein in Chemical Formula 1,
M is selected from the group consisting of rhodium (Rh), cobalt (Co), iridium (Ir), ruthenium (Ru), iron (Fe), nickel (Ni), palladium (Pd), platinum (Pt) and osmium (Os);
L1, L2 and L3 are the same as or different from each other, and are each independently selected from the group consisting of hydrogen, carbonyl (CO), cyclooctadiene, norbornene, chlorine, triphenylphosphine (TPP) and acetylacetonato (AcAc); and
x, y and z are each independently an integer of 0 to 5, and x, y and z are not 0 at the same time;
wherein the solvent comprises one or more selected from the group consisting of tetraethylene glycol dimethyl ether (TEGDME), 1,2,4-trimethylbenzene and cumene; and wherein the raw-C5 feed has a total weight ratio of less than 1,000 and the solvent has a total weight ratio of 500 or greater, based on a total weight of the transition metal compound.

2. The hydroformylation method of claim 1, wherein the raw-C5 feed is a product of a naphtha cracking center (NCC) process, and the raw-C5 feed comprises a mixture of a terminal monoene, an internal monoene and a diene.

3. The hydroformylation method of claim 2, wherein, an amount of the diene in the raw-C5 feed is 30% by weight or more based on a total weight of the mixture of the terminal monoene, internal monoene and diene.

4. The hydroformylation method of claim 1, wherein the phosphorous-based ligand comprises one or more selected from the group consisting of 1,2-bis(diphenylphosphino) ethane, 4,5-bis(diphenylphosphino), triphenylphosphine and 6,6'-[(3,3'-di-tert-butyl-5,5'-dimethoxy-1,1'-biphenyl-2,2'-diyl)bis(oxy) This(dibenzo[d,f][1,3,2]dioxaphosphephine).

5. The hydroformylation method of claim 1, wherein the transition metal compound comprises one or more selected from the group consisting of cobalt carbonyl [$CO_2(CO)_8$], acetylacetonatodicarbonyl rhodium [$Rh(AcAc)(CO)_2$], acetylacetonatocarbonyl triphenylphosphine rhodium [$Rh(AcAc)(CO)(TPP)$)], hydridocarbonyl tri(triphenylphosphine)rhodium [$HRh(C0)(TPP)_3$], acetylacetonatodicarbonyl iridium [$Ir(AcAc)(CO)_2$], hydridocarbonyl tri(triphenylphosphine)iridium [$HIr(CO)(TPP)_3$] and chloro(1,5-cyclooctadiene)rhodium [$Rh(COD)Cl_2$].

6. The hydroformylation method of claim 1, wherein the hydroformylation method is carried out at a reaction temperature of 90° C. or higher and a reaction pressure of 15 bar or higher.

7. The hydroformylation method of claim 1, wherein a molar ratio of the raw-C5 feed to the synthetic gas is from 95:5 to 5:95.

8. The hydroformylation method of claim 1, wherein the synthetic gas comprises carbon monoxide and hydrogen, in a molar ratio of from 5:95 to 70:30.

\* \* \* \* \*